· US 10,342,830 B2

(12) United States Patent
Petrucci

(10) Patent No.: US 10,342,830 B2
(45) Date of Patent: Jul. 9, 2019

(54) METHODS AND MATERIALS FOR TREATING LUNG DISORDERS

(71) Applicant: Gary M. Petrucci, Long Lake, MN (US)

(72) Inventor: Gary M. Petrucci, Long Lake, MN (US)

(*) Notice: Subject to any disclaimer, the term of this patent is extended or adjusted under 35 U.S.C. 154(b) by 0 days.

(21) Appl. No.: 14/984,738

(22) Filed: Dec. 30, 2015

(65) Prior Publication Data
US 2016/0193253 A1 Jul. 7, 2016

Related U.S. Application Data

(60) Provisional application No. 62/099,869, filed on Jan. 5, 2015, provisional application No. 62/166,233, filed on May 26, 2015, provisional application No. 62/240,076, filed on Oct. 12, 2015.

(51) Int. Cl.
*A61K 35/50* (2015.01)
*A61K 35/28* (2015.01)
*A61K 9/10* (2006.01)
*A61K 9/00* (2006.01)

(52) U.S. Cl.
CPC ............ *A61K 35/50* (2013.01); *A61K 9/0073* (2013.01); *A61K 9/10* (2013.01); *A61K 35/28* (2013.01)

(58) Field of Classification Search
CPC ...... A61K 35/50; A61K 9/0073; A61K 35/28; A61K 9/10
See application file for complete search history.

(56) References Cited

U.S. PATENT DOCUMENTS

| | | | |
|---|---|---|---|
| 4,828,844 A | 5/1989 | Rontgen-Odenthal et al. | |
| 5,049,389 A * | 9/1991 | Radhakrishnan | A61K 9/0078 264/4.1 |
| 5,131,907 A | 7/1992 | Williams | |
| 5,656,498 A | 8/1997 | Iijima et al. | |
| 5,674,192 A | 10/1997 | Sahatijan et al. | |
| 7,524,489 B2 | 4/2009 | Messina et al. | |
| 7,682,803 B2 | 3/2010 | Paludan et al. | |
| 8,323,701 B2 | 12/2012 | Daniel et al. | |
| 8,357,403 B2 | 1/2013 | Daniel et al. | |
| 8,372,437 B2 | 2/2013 | Daniel | |
| 8,372,438 B2 | 2/2013 | Daniel et al. | |
| 8,372,439 B2 | 2/2013 | Daniel et al. | |
| 8,409,626 B2 | 4/2013 | Daniel et al. | |
| 8,460,715 B2 | 6/2013 | Daniel | |
| 8,460,716 B2 | 6/2013 | Daniel | |
| 8,524,462 B2 | 9/2013 | Valkirs et al. | |
| 8,623,421 B2 | 1/2014 | Daniel | |
| 8,642,092 B2 | 2/2014 | Daniel et al. | |
| 8,703,206 B2 | 4/2014 | Daniel et al. | |
| 8,703,207 B2 | 4/2014 | Daniel et al. | |
| 8,709,493 B2 | 4/2014 | Daniel et al. | |
| 8,709,494 B2 | 4/2014 | Daniel | |
| 8,904,664 B2 | 12/2014 | Pringle et al. | |
| 8,932,643 B2 | 1/2015 | Daniel et al. | |
| 9,039,783 B2 | 5/2015 | Petter-Puchner | |
| 9,080,184 B2 | 7/2015 | Kharazi et al. | |
| 9,084,767 B2 | 7/2015 | Daniel et al. | |
| 9,180,145 B2 | 11/2015 | Brown et al. | |
| 9,186,382 B2 | 11/2015 | Daniel et al. | |
| 9,205,177 B2 | 12/2015 | Schorgl et al. | |
| 9,265,800 B2 | 2/2016 | Daniel | |
| 9,265,801 B2 | 2/2016 | Daniel | |
| 9,272,003 B2 | 3/2016 | Daniel et al. | |
| 9,272,005 B2 | 3/2016 | Daniel | |
| 9,415,074 B2 | 8/2016 | Daniel et al. | |
| 9,433,647 B2 | 9/2016 | Daniel | |
| 9,463,206 B2 | 10/2016 | Koob et al. | |
| 9,533,011 B2 | 1/2017 | Daniel et al. | |
| 9,555,062 B2 | 1/2017 | Pringle et al. | |
| 9,572,839 B2 | 2/2017 | Daniel | |
| 9,655,948 B1 | 5/2017 | Koob et al. | |
| 9,662,355 B2 | 5/2017 | Koob et al. | |
| 9,687,588 B2 | 6/2017 | Daniel et al. | |
| 9,789,137 B2 | 10/2017 | Daniel et al. | |
| 9,827,293 B2 | 11/2017 | Koob et al. | |
| 2003/0187515 A1 | 10/2003 | Hariri | |
| 2003/0229394 A1 | 12/2003 | Ogle et al. | |
| 2003/0235563 A1 | 12/2003 | Strom et al. | |
| 2003/0235580 A1 | 12/2003 | Zhang | |
| 2004/0147045 A1 * | 7/2004 | Nelson | B82Y 30/00 436/518 |
| 2005/0020500 A1 | 1/2005 | Shen et al. | |
| 2005/0287223 A1 | 12/2005 | Peyman | |
| 2006/0073592 A1 * | 4/2006 | Sun | A01N 1/00 435/423 |
| 2007/0031471 A1 * | 2/2007 | Peyman | A61L 27/3604 424/427 |
| 2007/0293872 A1 | 12/2007 | Peyman | |
| 2008/0181950 A1 | 7/2008 | Bates | |
| 2009/0125044 A1 | 5/2009 | Lary | |
| 2009/0238801 A1 | 9/2009 | Woodbury et al. | |
| 2009/0270978 A1 | 10/2009 | Virkler | |

(Continued)

FOREIGN PATENT DOCUMENTS

| | | |
|---|---|---|
| WO | WO 98/08492 | 5/1998 |
| WO | WO 2007/038686 | 4/2007 |
| WO | WO 2012/112410 | 8/2011 |
| WO | WO 2012/088396 | 6/2012 |
| WO | WO 2014/047067 | 3/2014 |
| WO | WO 2015/134936 | 9/2015 |
| WO | WO 2016/007554 | 1/2016 |
| WO | WO 2016/198670 | 12/2016 |

OTHER PUBLICATIONS

Chen et al., "The effects of acellular amniotic membrane matrix on osteogenic differenetiation and ERK1/2 signaling in human dental apical papilla cells," Biomaterials, 2012, 33(2): 455-63.

(Continued)

*Primary Examiner* — Mina Haghighatian
(74) *Attorney, Agent, or Firm* — Fish & Richardson P.C.

(57) ABSTRACT

This document provides methods and materials for treating lung conditions induced by inhalable insulin therapy. For example, compositions including a dried amnion tissue preparation and/or a dried stem cell preparation as well as methods for using such compositions to treat inhalable insulin induced lung conditions are provided.

8 Claims, No Drawings

(56) References Cited

U.S. PATENT DOCUMENTS

| | | | |
|---|---|---|---|
| 2010/0143312 A1* | 6/2010 | Hariri | C12N 5/0605 424/93.7 |
| 2010/0228335 A1* | 9/2010 | Schorgl | A61L 31/005 623/1.15 |
| 2010/0260721 A1 | 10/2010 | McGonagie et al. | |
| 2011/0307003 A1 | 12/2011 | Chambers | |
| 2012/0080030 A1 | 4/2012 | Wachter | |
| 2012/0171171 A1 | 7/2012 | West et al. | |
| 2012/0201787 A1 | 8/2012 | Abbot et al. | |
| 2012/0269785 A1 | 10/2012 | Woods et al. | |
| 2013/0071358 A1* | 3/2013 | Peterson | A61K 35/12 424/93.7 |
| 2013/0238100 A1 | 9/2013 | Young | |
| 2014/0236161 A1 | 8/2014 | Brahm | |
| 2014/0271776 A1 | 9/2014 | Vines | |
| 2015/0037436 A1 | 2/2015 | Huang et al. | |
| 2015/0216910 A1 | 8/2015 | Horton et al. | |
| 2015/0216912 A1 | 8/2015 | Koob | |
| 2016/0136334 A1 | 5/2016 | Schorgl et al. | |
| 2016/0184479 A1 | 6/2016 | Fette | |
| 2016/0193254 A1* | 7/2016 | Petrucci | A61K 35/50 424/93.7 |
| 2016/0199417 A1 | 7/2016 | Werber | |
| 2016/0199537 A1 | 7/2016 | Koob | |
| 2017/0042943 A1 | 2/2017 | Namin et al. | |

OTHER PUBLICATIONS

Diaz-Prado et al., "Human amniotic membrane as an alternative source of stem cells for regenerative medicine," Differentiation, 2011, 81(3): 162-71.
International Search Report and Written Opinion in International Application No. PCT/US2015/68127, dated Apr. 19, 2016, 18 pages.
International Search Report and Written Opinion in International Application No. PCT/US2015/68136, dated Feb. 26, 2016, 13 pages.
McDonald et al., "Maintenance of human amnion epithelial cell phenotype in pulmonary surfactant," Stem Cell Research & Therapy, 2014, 5: 107.
Orth et al., "Current perspectives in stem cell research for knee cartilage repair," Stem Cells Cloning, Jan. 2014, 7: 1-17.
Wilshaw et al., "Production of an acellular amniotic membrane matrix for use in tissue engineering," Tissue Eng., 2006, 12(8): 2117-29.
Lei et al., "Dehydrated Human Amnion/Chorion Membrane (dHACM) Allografts as a Therapy for Orthopedic Tissue Repair," Techniques in Orthopaedics, 2017, 9 pages.
International Preliminary Report on Patentability in Application No. PCT/US2015/068127, dated Jul. 11, 2017, 12 pages.
International Preliminary Report on Patentability in Application No. PCT/US2015/068136, dated Jul. 11, 2017, 11 pages.
"Angioplasty or bypass surgery?," Harvard Heart Letter, Apr. 2008, 2 pages.
Alkilani et al., "Transdermal Drug Delivery: Innovative Pharmaceutical Developments Based on Disruption of the Barrier Properties of the stratum corneum," Pharmaceutics, 2015, 7: 438-470.
Anand et al., "Use of amniotic membrane graft in glaucoma shunt surgery," Opthalmic Surg Lasers Imaging, May-Jun. 2011, 42: 184-9.
Brown et al., "Dermal and Transdermal Drug Delivery Systems: Current and Future Prospects," Drug Delivery, 2006, 13: 175-187.
Derdeyn et al. AJNR Am J Neuroradiol 18:647-653, Apr. 1997.
Dhote et al., "Iontophoresis: A Potential Emergence of a Transdermal Drug Delivery System," Sci Pahrm, 2012, 80: 1-28.
Gerth et al., "Clinical outcomes for Conduits and Scaffolds in peripheral nerve repair," Worls J Clin Cases, Feb. 2015, 3: 141-147.
Hassan et al., "Neural-Differentiated Mesenchymal Stem Cells Incorporated into Muscle Stuffed Vein Scaffold Forms a Stable Living Nerve Conduit," Journal of Orthopaedic Research, Oct. 2012, 1674-1681.
International Search report and Written Opinion in International Application No. PCT/2017/016225, dated Apr. 14, 2017, 18 pages.
Kalluri and Banga, "Transdermal Delivery of Proteins," AAPS PharmSciTech, Mar. 2011, 12: 431-441.
Khan et al., "Iontophoretic drug delivery: History and applications," Journal of Applied Pharmaceutical Science, 2011, 11-24.
Kumar and Philip, "Modified Transdermal Technologies: Breaking the Barriers of Drug Permeation via the Skin," Tropical Journal of Pharmaceutical research, Mar. 2007, 6: 633-644.
Liu, "[Shunt tube implantation combining amniotic membrane transplantation and implantation of Molteno implant for glaucoma after penetrating keratoplasty]," Yan Ke Xue Bao, Jun. 2000, 16: 65-72, abstract only.
Quint et al., "Decellularized tissue-engineered blood vessel as an arterial conduit," PNAS, May 2011, 108: 9214-9219.
Sabongi et al., "Peripheral nerve regeneration with conduits: use of vein tubes," Neural regen Res, Apr. 2015, 10: 529-533.
Vaidya et al., "An Overview of Embolic Agents," Seminars in Interventional Radiology, 2008, 25: 204-215.
Zhan et al., "Nanofiber scaffolds facilitate functional regeneration of peripheral nerve injury," Nanomedicine, 2013, 9: 305-315.
Harvard Men's Health Watch, "The crucial, controversial carotid artery Part I: The artery in health and disease," Harvard Health Publishing, Aug. 2011, 6 pages.
International Search Report & Written Opinion in International Application No. PCT/US2018/051651 dated Dec. 6, 2018, 20 pages.
International Search report and Written Opinion in International Application No. PCT/US 18/38815, dated Sep. 19, 2018, 16 pages.
Interntional Preliminary Report on Patentability in International Application No. PCT/US2017/016225, dated Aug. 16, 2018.
Robertson et al., "Angioplasty and stenting for peripheral arterial disease of the lower limbs: an overview of Cochrane Reviews (Protocol)," Cochrane Database of Systematic Reviews, Feb. 2017, 2: CD012542 (11 pages).

* cited by examiner

METHODS AND MATERIALS FOR TREATING LUNG DISORDERS

CLAIM OF PRIORITY

This application claims priority to U.S. Provisional Application Ser. No. 62/099,869 filed Jan. 5, 2015, U.S. Provisional Application Ser. No. 62/166,233 filed May 26, 2015, and U.S. Provisional Application Ser. No. 62/240,076 filed Oct. 12, 2105, the entire contents of which are hereby incorporated by reference.

BACKGROUND

1. Technical Field

This document relates to methods and materials for treating lung disorders (e.g., lung disorders induced by treatment with inhalable insulin or exercise-induced pulmonary hemorrhage). For example, this document provides methods and materials for using compositions (e.g., inhalable formulations) that include a dried amnion tissue preparation and/or a dried stem cell preparation to treat lung disorders induced by inhalable insulin therapy. This document also provides methods and materials for using compositions (e.g., inhalable formulations) that include a dried amnion tissue preparation and/or a dried stem cell preparation in combination with an inhalable insulin therapy to reduce or prevent development of lung disorders induced by inhalable insulin therapy. This document also provides methods and materials for using compositions (e.g., inhalable formulations) that include a dried amnion tissue preparation and/or a dried stem cell preparation to treat lung disorders such as exercise-induced pulmonary hemorrhage.

2. Background Information

Inhalable insulin (Afrezza®) is a rapidly acting form of insulin that patients with Type 1 or Type 2 diabetes can use to help with glycemic control. Afreeza® can cause a decline in lung function over time as measured by forced expiratory volume ($FEV_1$) and common adverse reactions include cough, and throat pain or irritation. Afreeza® also is contraindicated in patients with chronic lung disease (e.g., asthma, chronic obstructive pulmonary disease (COPD), or other chronic lung disease(s)). See, package insert for Afreeza®.

Exercise-induced pulmonary hemorrhage is a medical condition that refers to the presence of blood in lung airways in association with exercise. In some cases, between about 40 to 70 percent of horses may experience blood in the trachea following a horse race.

SUMMARY

This document provides methods for using compositions (e.g., inhalable formulations) that include a dried amnion tissue preparation, a dried stem cell preparation, or both in combination, to treat lung disorders induced by inhalable insulin therapy. Such compositions can be formulated for inhalation and used to treat any type of lung disorder induced by inhalable insulin therapy. For example, the compositions can be used to treat bronchospasms, asthma, COPD, chronic bronchitis, emphysema, pulmonary hypertension, asthma, interstitial lung disease, acute respiratory distress syndrome, pneumonia, lung infections, or pulmonary fibrosis that may be induced by inhalable insulin therapy.

This document also provides methods and materials for using compositions (e.g., inhalable formulations) that include a dried amnion tissue preparation and/or a dried stem cell preparation in combination with an inhalable insulin therapy to reduce or prevent development of lung disorders induced by inhalable insulin therapy. For example, a mammal (e.g., human) needing or desiring to take an inhalable insulin therapy (e.g., Afrezza®; MannKind Corp.) can be instructed to take a composition (e.g., inhalable formulations) that includes a dried amnion tissue preparation, a dried stem cell preparation, or both to reduce or prevent development of lung disorders induced by inhalable insulin therapy. In some cases, a mammal (e.g., a human) with a lung disorder such as asthma and chronic obstructive pulmonary disease who is warned not to administer an inhalable insulin therapy because of that lung disorder can be treated with a composition (e.g., inhalable formulation) that includes a dried amnion tissue preparation and/or a dried stem cell preparation either as an initial treatment or as a combination treatment together with an inhalable insulin therapy. After the initial treatment with a composition (e.g., inhalable formulation) that includes a dried amnion tissue preparation and/or a dried stem cell preparation, the mammal can be treated with an inhalable insulin therapy.

In another aspect, this document provides methods for using compositions (e.g., inhalable formulations) that include a dried amnion tissue preparation, a dried stem cell preparation, or both in combination, to treat lung disorders such as exercise-induced pulmonary hemorrhage. Such compositions can be formulated for inhalation and used to treat any type of exercise-induced pulmonary hemorrhage. For example, the compositions can be used to treat pulmonary hemorrhage that may be induced racing or athletic activities. In some cases, a mammal (e.g., human, dog, or horse) suffering from or suspected of suffering from exercise-induced pulmonary hemorrhage can be instructed to take a composition (e.g., inhalable formulations) that includes a dried amnion tissue preparation, a dried stem cell preparation, or both to reduce or prevent development of exercise-induced pulmonary hemorrhage.

In general, one aspect of this document features a method of treating a mammal having a lung disorder induced by inhalable insulin therapy. The method comprises, or consists essentially of, administering, to the mammal via inhalation, a composition comprising a dried amnion tissue preparation lacking viable cells or a dried stem cell preparation lacking viable cells. The lung disorder can be asthma, chronic obstructive pulmonary disease, chronic bronchitis, emphysema, pulmonary hypertension, interstitial lung disease, acute respiratory distress syndrome, pneumonia, a lung infection, or pulmonary fibrosis. The lung disorder can include bronchospasms. The composition can comprise the dried amnion tissue preparation and the dried stem cell preparation. The composition can comprise a therapeutic agent, a growth factor, a polymer, a lipopolymer, a lung surfactant, or a pharmaceutical excipient. The composition can comprise the lung surfactant. The lung surfactant can be dipalmitoylphosphatidyl-choline (DPPC). The composition can comprise a pharmaceutical excipient. The composition can comprise a growth factor. The method can comprise monitoring lung function of the mammal. The composition can comprise the dried amnion tissue preparation. The dried amnion tissue preparation can comprise a dried amnion tissue preparation prepared from about 1 mg to about 10 g of amnion tissue per kg of body weight of the mammal. The composition can comprise the dried stem cell preparation. The dried stem cell preparation can comprise a dried stem cell preparation prepared from about 0.3 million to about 3 million stem cells per kg of body weight of the mammal. The dried amnion tissue preparation can be a human dried amnion tissue preparation. The dried stem cell preparation can be a human dried mesenchymal stem cell preparation.

In another aspect, this document features a method of treating a mammal needing insulin in a manner that reduces the risk of developing a lung disorder induced by inhalable insulin therapy. The method comprises, or consists essentially of, (a) administering, to the mammal via inhalation, insulin, and (b) administering, to the mammal via inhalation, a composition comprising a dried amnion tissue preparation lacking viable cells or a dried stem cell preparation lacking viable cells, wherein administration of the composition reduces the development of a lung disorder induced by the administering of the insulin in step (a). The lung disorder can be asthma or chronic obstructive pulmonary disease. The composition can comprise the dried amnion tissue preparation and the dried stem cell preparation. The composition can further comprise a therapeutic agent, a growth factor, a polymer, a lipopolymer, a lung surfactant, or a pharmaceutical excipient. The composition can comprise the lung surfactant. The lung surfactant can be DPPC. The composition can comprise the pharmaceutical excipient. The composition can comprise the growth factor. The method can further comprise monitoring lung function of the mammal. The composition can comprise the dried amnion tissue preparation. The dried amnion tissue preparation can comprise a dried amnion tissue preparation prepared from about 1 mg to about 10 g of amnion tissue per kg of body weight of the mammal. The composition can comprise the dried stem cell preparation. The dried stem cell preparation can comprise a dried stem cell preparation prepared from about 0.3 million to about 3 million stem cells per kg of body weight of the mammal. The dried amnion tissue preparation can be a human dried amnion tissue preparation. The dried stem cell preparation can be a human dried mesenchymal stem cell preparation.

In another aspect, this document features a method of treating a mammal needing insulin and having a lung disorder limiting the use of inhalable insulin. The method comprises, or consists essentially of, (a) administering, to the mammal via inhalation, a composition comprising a dried amnion tissue preparation lacking viable cells or a dried stem cell preparation lacking viable cells, wherein administration of the composition reduces the symptoms of the lung disorder, and (b) administering, to the mammal via inhalation, insulin. The lung disorder can be asthma or chronic obstructive pulmonary disease. The composition can comprise the dried amnion tissue preparation and the dried stem cell preparation. The composition can further comprise a therapeutic agent, a growth factor, a polymer, a lipopolymer, a lung surfactant, or a pharmaceutical excipient. The method can further comprise monitoring lung function of the mammal. The composition can comprise the dried amnion tissue preparation. The dried amnion tissue preparation can comprise a dried amnion tissue preparation prepared from about 1 mg to about 10 g of amnion tissue per kg of body weight of the mammal. The composition can comprise the dried stem cell preparation. The dried stem cell preparation can comprise a dried stem cell preparation prepared from about 0.3 million to about 3 million stem cells per kg of body weight of the mammal. The dried amnion tissue preparation can be a human dried amnion tissue preparation. The dried stem cell preparation can be a human dried mesenchymal stem cell preparation.

In another aspect, this document features a method of treating a mammal having exercise-induced pulmonary hemorrhage. The method comprises, or consists essentially of, administering, to the mammal via inhalation, a composition comprising a dried amnion tissue preparation lacking viable cells or a dried stem cell preparation lacking viable cells. The mammal can be a horse. The mammal can be a racing horse. The composition can comprise the dried amnion tissue preparation and the dried stem cell preparation. The composition can further comprise a therapeutic agent, a growth factor, a polymer, a lipopolymer, a lung surfactant, or a pharmaceutical excipient. The composition can comprise the lung surfactant. The lung surfactant can be dipalmitoylphosphatidyl-choline (DPPC). The composition can comprise the pharmaceutical excipient. The composition can comprise the growth factor. The method can further comprise monitoring a lung of the mammal for bleeding. The composition can comprise the dried amnion tissue preparation. The dried amnion tissue preparation can comprise a dried amnion tissue preparation prepared from about 1 mg to about 10 g of amnion tissue per kg of body weight of the mammal. The composition can comprise the dried stem cell preparation. The dried stem cell preparation can comprise a dried stem cell preparation prepared from about 0.3 million to about 3 million stem cells per kg of body weight of the mammal. The dried amnion tissue preparation can be a horse dried amnion tissue preparation. The dried stem cell preparation can be a horse dried mesenchymal stem cell preparation.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DETAILED DESCRIPTION

In general, this document provides methods and materials for treating lung disorders and conditions induced by inhalable insulin (e.g., Afrezza®) therapy using compositions that include a dried amnion tissue preparation (e.g., dried human amnion tissue preparation) and/or a dried stem cell preparation. Such lung disorders and conditions can include bronchospasms, COPD, chronic bronchitis, asthma, emphysema, pulmonary hypertension, interstitial lung disease, pulmonary fibrosis, pneumonia, lung infections, or acute respiratory distress syndrome.

This document also provides methods and materials for using compositions (e.g., inhalable formulations) that include a dried amnion tissue preparation and/or a dried stem cell preparation in combination with an inhalable insulin therapy to reduce or prevent development of lung disorders induced by inhalable insulin therapy. In some cases, a mammal (e.g., a human) with a lung disorder such as asthma and chronic obstructive pulmonary disease who is warned not to administer an inhalable insulin therapy because of that lung disorder can be treated with a composition (e.g., inhalable formulation) that includes a dried amnion tissue preparation and/or a dried stem cell preparation either as an initial treatment or as a combination treatment together with an inhalable insulin therapy. After the initial treatment with a composition (e.g., inhalable formulation) that includes a dried amnion tissue preparation and/or a dried stem cell preparation, the mammal can be treated with an inhalable insulin therapy.

In some cases, a composition (e.g., an inhalable formulation) that includes a dried amnion tissue preparation and/or a dried stem cell preparation can be administered to humans who smoke tobacco products (e.g., cigarettes, cigars, or pipes) or to humans with a history of smoking tobacco products (e.g., cigarettes, cigars, or pipes) to reduce the severity of symptoms (e.g., lung symptoms) of smoking or to reduce the development of symptoms (e.g., lung symptoms) of smoking. For example, a human who smokes cigarettes can be administered a composition (e.g., an inhalable formulation) that includes a dried amnion tissue preparation and/or a dried stem cell preparation to reduce the severity of a chronic smoker's cough, a gravelly voice, and/or shortness of breath.

In another aspect, this document provides methods and materials for treating lung disorders and conditions such as exercise-induced pulmonary hemorrhage using compositions that include a dried amnion tissue preparation (e.g., dried human amnion tissue preparation) and/or a dried stem cell preparation.

In some cases, a composition (e.g., an inhalable formulation) that includes a dried amnion tissue preparation and/or a dried stem cell preparation can be administered to a mammal suffering from or suspected to suffer from exercise-induced pulmonary hemorrhage. Examples of such mammals include, without limitation, horses (e.g., race horses), dogs (e.g., racing dogs), or humans (e.g., human athletes).

The term "dried amnion tissue preparation" as used herein refers to a preparation of amnion tissue or amnion material that is dried to have a water content that is less than about 8 percent (e.g., less than about 7 percent, less than about 6 percent, less than about 5 percent, less than about 4 percent, less than about 3 percent, less than about 2 percent, or less than about 1 percent). The term "dried stem cell preparation" as used herein refers to a preparation of stem cells or stem cell material that is dried to have a water content that is less than about 8 percent (e.g., less than about 7 percent, less than about 6 percent, less than about 5 percent, less than about 4 percent, less than about 3 percent, less than about 2 percent, or less than about 1 percent). In some cases, a dried amnion tissue preparation or a dried stem cell preparation can have a water content that is between about 0.1 percent and about 8 percent (e.g., between about 0.5 percent and about 8 percent, between about 1 percent and about 8 percent, between about 0.1 percent and about 5 percent, between about 0.1 percent and about 4 percent, between about 0.1 percent and about 3 percent, between about 0.5 percent and about 5 percent, or between about 1 percent and about 4 percent). An amnion tissue preparation or stem cell preparation can be dried using any appropriate technique such as micronization, vacuum drying, spray drying, freeze drying, or combinations thereof. In some cases, an amnion tissue preparation or stem cell preparation can be dried as described elsewhere (e.g., U.S. Pat. No. 5,656,498).

A dried amnion tissue preparation can contain viable cells, non-viable cells, or a combination thereof. For example, a dried amnion tissue preparation can be a preparation of amnion tissue or amnion material where all the cells were removed, killed, or lysed such that the dried amnion tissue preparation lacks viable cells. In some cases, a dried amnion tissue preparation can be a preparation of amnion tissue or amnion material that was exposed to one or more physical and/or chemical treatments that killed, fixed, or lysed the cells of the amnion tissue or amnion material such that the dried amnion tissue preparation lacks viable cells. For example, temperature (e.g., rapid freezing or rapid freezing-thawing), force and pressure, and/or electrical disruption can be used to kill or lyse cells within amnion tissue or amnion material to produce a dried amnion tissue preparation that lacks viable cells.

In some cases, amnion tissue or amnion material can be obtained and then treated in a manner designed to lyse all the cells within the amnion tissue or amnion material. In these cases, the resulting material (e.g., matrix material and cellular remnants from lysed cells) can be dried to form a dried amnion tissue preparation that lacks viable cells.

In some cases, a dried amnion preparation can be prepared from human amnion tissue. For example, human amnion tissue can be harvested, processed to remove, kill, or lyse cells or to remove blood, and dried to form a dried amnion tissue preparation. In some cases, human amnion tissue can be processed to remove blood prior to forming a dried amnion tissue preparation. In some cases, human amnion tissue can be processed without removing cells or blood prior to forming a dried amnion tissue preparation.

An example of a dried amnion tissue preparation includes, without limitation, a dried human amnion tissue preparation that lacks viable cells. In some cases, a dried amnion tissue preparation can be obtained from MiMedX® or a tissue bank (e.g., a human tissue bank).

In some cases, an amnion tissue preparation containing viable cells can be used in place of or in addition to a dried amnion tissue preparation lacking viable cells to treat a lung disorder or condition such as exercise-induced pulmonary hemorrhage.

A dried stem cell preparation can contain viable stem cells, non-viable stem cells, or a combination thereof. For example, a dried stem cell preparation can be a preparation of stem cell or stem cell material where all the stem cells were killed, fixed, or lysed such that the dried stem cell preparation lacks viable stem cells. In some cases, a dried stem cell preparation can be a preparation of stem cells or stem cell material that was exposed to one or more physical and/or chemical treatments that killed, fixed, or lysed the stem cells such that the dried stem cell preparation lacks viable stem cells. For example, temperature (e.g., rapid freezing or rapid freezing-thawing), force and pressure, and/or electrical disruption can be used to kill or lyse stem cells to produce a dried stem cell preparation that lacks viable stem cells.

In some cases, a stem cell culture can be obtained and then treated in a manner designed to lyse all the stem cells. In these cases, the resulting material (e.g., cellular remnants from lysed stem cells) can be dried to form a dried stem cell preparation that lacks viable stem cells.

Examples of dried stem cell preparations include, without limitation, a dried lung stem cell preparation such as a lung epithelial progenitor cell preparation, a dried mesenchymal stem cell (MSC) preparation (e.g., a MSC preparation obtained from fat tissue or bone marrow), a dried umbilical cord blood stem cell preparation, a dried embryonic stem cell preparation, and a dried human induced pluripotent stem cell preparation.

In some cases, dried stem cell preparations are prepared from cultures of stem cells. For example, a culture containing from about 25 million to about 25 billion stem cells can be used to make a dried stem cell preparation. In some cases, from about 0.3 million to about 3 million (e.g., from about 0.3 million to about 3 million, from about 0.5 million to about 3 million, from about 0.75 million to about 3 million, from about 1 million to about 3 million, from about 1.5 million to about 3 million, from about 0.3 million to about 2.5 million, from about 0.3 million to about 2.0 million, from about 0.3 million to about 1.5 million, from about 0.3 million to about 1.0 million, from about 0.5 million to about 2.5 million, from about 0.75 million to about 2.0 million, from about 0.8 million to about 1.5 million) stem cells per kg of body weight of a mammal (e.g., a human) to be treated can be used to make a dried stem cell preparation for administration to that mammal. In some cases, a dried stem cell preparation can be obtained commercially from Stemedica Cell Technologies, Inc.

In some cases, a dried stem cell preparation can be prepared by washing a culture of stem cells in saline (e.g., phosphate buffered saline) to remove culture medium, evaporating to remove wash medium, adding a solution (e.g., saline, water, or a water and sugar solution) to the resulting stem cell preparation, and repeating the evaporation step. After the second evaporation step, the stem cell preparation can be formulated into a powder that can be used as a dried stem cell preparation.

In some cases, a stem cell tissue preparation containing viable cells can be used in place of or in addition to a dried stem cell preparation lacking viable cells to treat a lung disorder or condition such as exercise-induced pulmonary hemorrhage.

Typically, a composition described herein (e.g., a composition containing a dried amnion tissue preparation, a dried stem cell preparation, or both a dried amnion tissue preparation and a dried stem cell preparation) is administered via inhalation, and the dried amnion tissue preparation and/or dried stem cell preparation will have a particle size suitable for delivery to the respiratory tract of a user (e.g., a mammal such as a human, dog, cat, horse, cow, pig, sheep, goat, or monkey). For example, the dried amnion tissue preparation and/or dried stem cell preparation can have a particle size ranging from about 0.1 µm to about 25 µm (e.g., from about 0.5 µm to about 25 µm, from about 0.75 µm to about 25 µm, from about 1 µm to about 25 µm, from about 0.1 µm to about 15 µm, from about 0.1 µm to about 10 µm from about 0.1 µm to about 7.5 µm from about 0.1 µm to about 5 µm from about 0.75 µm to about 7.5 µm or from about 1 µm to about 5 µm).

In some cases, a dried amnion tissue preparation and/or a dried stem cell preparation can have a particle size suitable for delivery to the upper respiratory tract (URT). The URT includes the nose, sinuses, pharynx and larynx. For example, a dried amnion tissue preparation and/or a dried stem cell preparation having a particle size ranging from about 5 µm to about 25 µm from about 5 µm to about 15 µm, or from about 5 µm to about 10 µm can be used to treat a disorder of the URT.

In some cases, a dried amnion tissue preparation and/or a dried stem cell preparation can have a particle size suitable for delivery to the lower respiratory tract (LRT), which includes the trachea, upper bronchi, and lungs, and be used to treat a lung disorder such as exercise-induced pulmonary hemorrhage. For example, a dried amnion tissue preparation and/or a dried stem cell preparation having a particle size ranging from about 0.1 µm to about 5 µm (e.g., from about 0.5 µm to about 5 µm, from about 0.75 µm to about 5 µm from about 1 µm to about 5 µm from about 0.1 µm to about 2 µm from about 0.1 µm to about 1 µm from about 0.1 µm to about 0.75 µm) can be used to treat a lung disorder such as exercise-induced pulmonary hemorrhage.

In some cases, a composition that includes a dried amnion tissue preparation and/or a dried stem cell preparation also can include one or more therapeutic agents, one or more anti-inflammatory agents (e.g., non-steroidal anti-inflammatory drugs, dexamethasone or other type of glucocorticoid steroids), one or more growth factors (e.g., platelet derived growth factor PDGF, epithelial growth factor (EGF), fibroblast growth factor-2 (FGF2), or stem cell factor (SCF)), one or more lung surfactants (e.g., DPPC), and/or one or more antimicrobial agents (e.g., antibiotics such as kanamycin, neomycin, streptomycin, or gentamicin or an antifungal agent).

Compositions containing a dried amnion tissue preparation and/or a dried stem cell preparation can be formulated as inhalable compositions using one or more pharmaceutically acceptable carriers or excipients. In some cases, a dried amnion tissue preparation and/or a dried stem cell preparation can be formulated into microparticles that contain solid lipid nanoparticles. In some cases, the particles of a dried amnion tissue preparation and/or a dried stem cell preparation can be coated or encapsulated for delivery to an airway (e.g., a lung) via an aerosol based inhaler or a dry powder inhaler.

As described herein, lung disorders can be treated by administering (e.g., via inhalation) an effective amount of a composition that includes a dried amnion tissue preparation described herein and/or a dried stem cell preparation described herein. Effective amounts of compositions described herein can be determined by a physician, taking into account various factors such as overall health status, body weight, sex, diet, time and route of administration, other medications, and any other relevant clinical factors. As used herein, an "effective amount" or "therapeutically effective amount" of a composition is the amount that is sufficient to provide a beneficial effect to the subject to which the composition or preparations are delivered. The effective amount can be the amount effective to achieve an improved survival rate, a more rapid recovery, an improvement in the quality of life, or an improvement or elimination of one or more symptoms associated with a subject's lung disorder (e.g., exercise-induced pulmonary hemorrhage).

In some embodiments, the methods include delivering, to the subject, a dried amnion tissue preparation made with from about 0.01 mg to about 10 g (e.g., from about 0.01 mg to about 10 g, from about 0.1 mg to about 10 g, from about 1 mg to about 10 g, from about 10 mg to about 10 g, from about 100 mg to about 10 g, from about 1 g to about 10 g, from about 0.01 mg to about 5 g, from about 0.01 mg to about 1 g, from about 0.01 mg to about 100 mg, from about 10 mg to about 5 g, from about 100 mg to about 1 g, or from about 1 g to about 5 g) of amnion tissue per kg body weight of the subject being treated.

In some embodiments, the methods include delivering, to the subject, a dried stem cell preparation made from about 0.3 million to about 3 million (e.g., from about 0.5 million to about 3 million, from about 0.75 million to about 3 million, from about 1 million to about 3 million, from about 1.5 million to about 3 million, from about 0.3 million to about 2.5 million, from about 0.3 million to about 2.0 million, from about 0.3 million to about 1.5 million, from about 0.3 million to about 1.0 million, from about 0.5 million to about 2.5 million, from about 0.75 million to about 2.0 million, from about 0.8 million to about 1.5 million) stem cells per kg body weight of the subject being treated.

In some embodiments, the compositions containing a dried amnion tissue preparation described herein and/or a dried stem cell preparation described herein are delivered to the subject by inhalation only once. In some embodiments, multiple (e.g., two, three, four, five, six, seven, eight, nine, 10, 11, 12, 13, 14, 15, or 20 or more) deliveries are made by inhalation. For example, multiple deliveries of a dried amnion tissue preparation described herein and/or a dried stem cell preparation described herein can be made over the course of several (e.g., two, three, four, five, six, seven, eight, nine, 10, 14, 21, 28, or 31 or more) consecutive days (e.g., one delivery each day for seven days or one delivery every other day for seven days). In some cases, a dried amnion tissue preparation described herein and/or a dried stem cell preparation described herein can be delivered from about two to four times a day to about once per month. In some cases, a dried amnion tissue preparation described herein and/or a dried stem cell preparation described herein can be delivered to a subject for several months (e.g., one delivery per month for six months, or one delivery per week for two months).

A dried amnion tissue preparation described herein and/or a dried stem cell preparation described herein can be delivered to a subject at various time points after diagnosis with a lung disorder (e.g., exercise-induced pulmonary hemorrhage). For example, a dried amnion tissue preparation described herein and/or a dried stem cell preparation described herein can be delivered immediately following diagnosis of a lung disorder (e.g., exercise-induced pulmonary hemorrhage). In some cases, a dried amnion tissue preparation described herein and/or a dried stem cell preparation described herein can be delivered to a subject less than 10 (e.g., 9, 8, 7, 6, 5, 4, 3, 2, or 1) days after diagnosis with a lung disorder (e.g., exercise-induced pulmonary hemorrhage).

The subject can be any mammal, e.g., a human (e.g., a human patient) or a non-human primate (e.g., chimpanzee, baboon, or monkey), a mouse, a rat, a rabbit, a guinea pig, a gerbil, a hamster, a horse, a type of livestock (e.g., cow, pig, sheep, or goat), a dog, or a cat. In some cases, the subject can be any appropriate mammal such as a human (e.g., a human athlete), a horse (e.g., a racing horse), or a dog (e.g., a racing dog) when treating exercise-induced pulmonary hemorrhage.

A composition described herein can be administered to a subject as a combination therapy with another treatment used to treat a lung disorder. For example, the combination therapy can include administering to the subject (e.g., a human patient) one or more additional agents that provide a therapeutic benefit to the subject who has, or is at risk of developing a lung disorder. In some cases, the composition and the one or more additional agents can be administered at the same time. In some cases, the composition can be administered first, and the one or more additional agents administered second, or vice versa.

The efficacy of a given treatment in treating a particular lung disorder can be defined as an improvement of one or more symptoms of the lung disorder by at least 5% (e.g., at least 10%, at least 15%, at least 20%, at least 25%, at least 30%, at least 40%, at least 50%, at least 55%, at least 60%, at least 65% or more). In some cases, efficacy of a treatment with a composition containing a dried amnion tissue preparation and/or a dried stem cell preparation can be determined from the stabilization of one or more symptoms associated with the lung disorder (i.e., the treatments curtail the worsening of one or more symptoms of the lung disorder).

In some cases, the methods described herein can include monitoring the lung disorder in the subject to, for example, determine if the disorder is improving with treatment. Any appropriate method can be used to monitor a lung disorder. For example, for COPD patients, lung function (e.g., using a spirometer or arterial blood gas test) can be monitored. For exercise-induced pulmonary hemorrhage patients, clinical techniques designed to detect the presence of blood in lung airways can be used.

Compositions that include a dried amnion tissue preparation described herein and/or a dried stem cell preparation described herein can be combined with packaging material and sold as a kit. The packaging material included in a kit typically contains instructions or a label describing how the composition can be administered via inhalation. A kit also can include an inhaler such as a unit dose inhaler or a multiple dose inhaler. The term "unit dose inhaler" refers to an inhaler that delivers a single dose of a dry powder formulation by inhalation to a user. Typically, a unit dose inhaler contains a single container that holds or contains an inhalable formulation. It will be appreciated that in some cases, multiple unit doses are required to provide a user with a specified dosage. The term "multiple dose inhaler" refers to an inhaler having two or more containers, each container comprising a pre-metered dose of a dry powder medicament, and the inhaler delivers a single dose of a medicament powder by inhalation at any one time.

As used herein a "unit dose" refers to a pre-metered formulation (e.g., a dry powder formulation) for inhalation. In some cases, a unit dose can be a single container having multiple doses of formulation that can be delivered by inhalation as metered single amounts. A unit dose cartridge/container can contain a single dose. In some cases, it can include multiple individually accessible compartments, each containing a unit dose.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An inhaler selected from a metered dose inhaler and a dry powder inhaler, the inhaler comprising:
    a dried stem cell preparation lacking viable cells; and
    a dried amnion tissue preparation lacking viable cells, wherein said dried stem cell preparation is a dried umbilical cord-, fat tissue-, or bone marrow-derived stem cell preparation of cellular remnants from lysed stem cells.

2. The inhaler of claim 1, wherein said dried stem cell preparation is a dried umbilical cord-derived stem cell preparation.

3. The inhaler of claim 1, wherein said dried stem cell preparation and said dried amnion tissue preparation are in the form of particles ranging in size from about 0.1 µm to about 10 µm.

4. The inhaler of claim 1, wherein said dried stem cell preparation and said dried amnion tissue preparation are in the form of particles ranging in size from about 1 µm to about 5 µm.

5. The inhaler of claim 1, wherein said composition comprises from about 5 mg and about 5 g of said dried amnion tissue preparation.

6. The inhaler of claim 1, wherein said composition comprises from about 10 mg and about 1 g of said dried amnion tissue preparation.

7. The inhaler of claim 3, wherein the particles are coated or encapsulated.

8. The inhaler of claim 1, further comprising a therapeutic agent, a growth factor, a polymer, a lipopolymer, a lung surfactant, or a pharmaceutical excipient.

* * * * *